United States Patent [19]

Oki

[11] Patent Number: 5,242,831
[45] Date of Patent: Sep. 7, 1993

[54] METHOD FOR EVALUATING ROUGHNESS ON SILICON SUBSTRATE SURFACE

[75] Inventor: Ichiro Oki, Nara, Japan

[73] Assignee: Sharp Kabushiki Kaisha, Osaka, Japan

[21] Appl. No.: 909,746

[22] Filed: Jul. 7, 1992

[30] Foreign Application Priority Data

Jul. 10, 1991 [JP] Japan .................. 3-169543
Sep. 3, 1991 [JP] Japan .................. 3-222755

[51] Int. Cl.$^5$ .................................. G01N 31/02
[52] U.S. Cl. ................................. 436/5; 436/72; 436/124; 436/151; 73/104; 73/105
[58] Field of Search ............ 436/72, 151, 5, 124; 73/104, 105

[56] References Cited

U.S. PATENT DOCUMENTS

| | | |
|---|---|---|
| 4,105,508 | 8/1978 | Arod et al. ................. 436/151 X |
| 4,464,222 | 8/1984 | Gutsche ..................... 437/225 X |
| 4,638,552 | 1/1987 | Shimbo et al. .............. 437/225 X |
| 4,746,591 | 5/1988 | Sakaki et al. ............... 430/155 X |
| 4,851,370 | 7/1989 | Doklan et al. .............. 437/225 |
| 5,153,701 | 10/1992 | Roy ............................ 357/54 |

Primary Examiner—James C. Housel
Assistant Examiner—Harold Y. Pyon
Attorney, Agent, or Firm—Nixon & Vanderhye

[57] ABSTRACT

A method for evaluating surface micro roughness of a silicon substrate includes the steps of soaking the silicon substrate in a mixture of hydrochloric acid of 30 to 40 vol %, hydrogen peroxide solution of 30 to 40 vol % and deionized water whose volume ratio is approximately 1:1:16.7, and measuring an amount of chlorine element incorporated into native oxide film on the silicon surface through the soaking process to evaluate the degree of the micro roughness on the silicon substrate surface.

6 Claims, 3 Drawing Sheets

Figure 2. Block diagram of the SCA system.

METHOD FOR EVALUATING ROUGHNESS ON SILICON SUBSTRATE SURFACE

BACKGROUND OF THE INVENTION

1. Field of the Invention

The present invention relates to a method for evaluating roughness on a silicon substrate surface with nanometer scale resolution.

2. Description of the Related Art

Roughness on a silicon substrate degrades electrical properties of a thin oxide films. Therefore, it is necessary to control and evaluate the surface roughness with nanometer scale resolution when a highly integrated circuit is manufactured. Conventionally, the surface roughness of the silicon substrate is evaluated by observing a cross section of the substrate using a scanning electron microscope (SEM) or a transmission electron microscope (TEM), or by scanning the substrate surface using a probe of a scanning tunneling microscope (STM) or an atomic force microscope (AFM).

According to the conventional methods, a region in which the surface roughness can be evaluated is small. For example, when the surface roughness is evaluated with nanometer scale resolution using the SEM or TEM, the sectional region which can be observed at one time is approximately several hundreds Å. In a case of using the STM or AFM which scan the surface with the probe, a region of only several tens μm square is measured, so that it is difficult to evaluate the surface roughness with nanometer scale resolution over a large area.

SUMMARY OF THE INVENTION

The present invention relates to a method for evaluating micro roughness on a silicon substrate surface by soaking the silicon substrate in a mixture of hydrochloric acid and hydrogen peroxide solution and then measuring an amount of a chlorine element deposited on the silicon surface through the soaking.

There are two methods for measuring the amount of the chlorine element. One is directly to measure the amount of the chlorine element itself by using total reflection X-ray fluorescence analysis or X-ray micro analyzer. Another is indirectly to measure an amount of the electric charge caused by chlorine ion incorporated into an native oxide film by using a surface charge analyzer.

DETAILED DESCRIPTION OF THE PREFERRED EMBODIMENT

A silicon substrate to be measured according to the present invention is a raw material used for a semiconductor manufacturing. For example, the substrate is (100) p-type doped silicon wafers with a 150 mm diameter.

The substrate is soaked in a mixture of hydrochloric acid and hydrogen peroxide solution. A temperature when it is soaked is preferably a room temperature (for example, 25° to 40° C.). Although a soaking period of time depends on the concentration of hydrochloric acid and hydrogen peroxide solution in the mixture and also depends on the temperature at the time of soaking, it is ordinarily approximately 5 to 20 minutes (for example, approximately 10 minutes).

The concentration of hydrochloric acid in the mixture is preferably 30 to 40 vol % (for example, 30 vol %). In addition, the concentration of hydrogen peroxide solution is preferably 30 to 40 vol % (for example, 30 vol %). Although a mixing ratio of those reagents and deionized water depends on the concentration of each reagent, the soaking temperature or the soaking period of time, it is, for example approximately 1:1:16.7 in regard to volume ratio.

The silicon substrate after soaked is rinsed in water and dried (for example, by a spin-dry method) and the chlorine element is measured. More specifically, through the soaking process, an native oxide film having a thickness of approximately 10 Å, oxidized by the hydrogen peroxide/hydrochloric acid solution, is formed on the surface of the silicon substrate and chlorine is incorporated into the oxide film. The substantial surface area is increased as the micro roughness of the silicon substrate to be measured is increased. Therefore, the amount of chlorine element which is incorporated into the substrate per the unit area is increased as the micro roughness is increased. The above fact is assured by the following preparatory experiment.

The amount of chlorine element can be measured using total reflection X-ray fluorescence analysis, X-ray micro analyzer or atomic absorption spectrometry. These methods directly measure the amount of the chlorine element itself. Meanwhile, the micro roughness can be evaluated by measuring an amount of the electric charge in the oxide film and an interface trap density at an interface between the oxide film and the silicon substrate by the surface charge analyzer.

REFERENCE EXAMPLE

In order to compare surface roughness measured by a conventional method (for example AFM method) with that measured by a method of the present invention, samples having different surface roughness are made by the following method.

Figure 1:
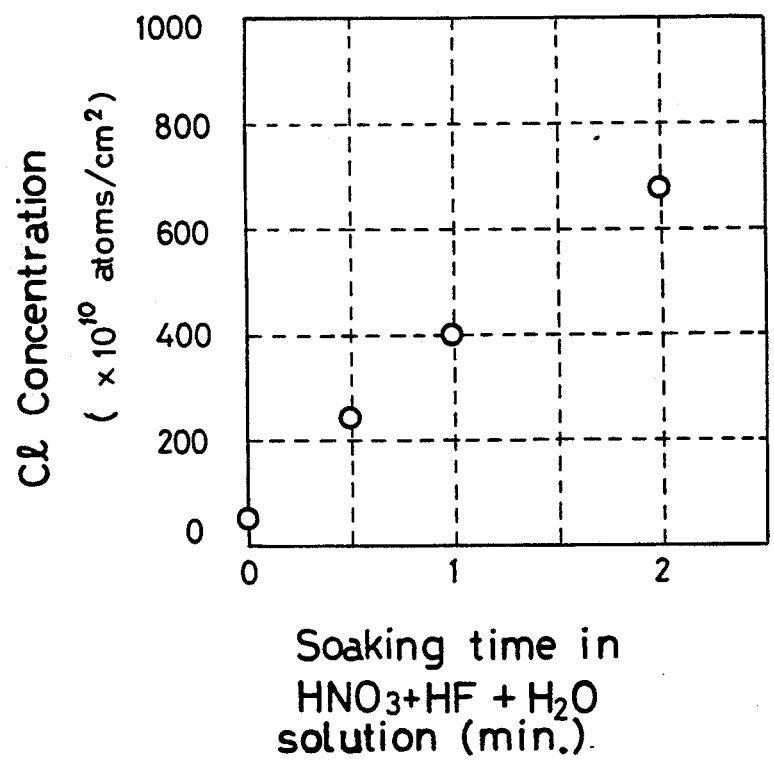
FIG. 1 is a chart showing a relation between a soaking period of time of a silicon substrate into a mixture of nitric acid and hydrofluoric acid and a concentration of chlorine ion on a surface of the silicon substrate.

A silicon substrate is soaked in a mixture of nitric acid (a concentration thereof is approximately 70 vol %), hydrofluoric acid (a concentration thereof is approximately 50 vol %) and deionized water at a room temperature in order to etch the silicon surface. The mixing ratio at this time is approximately 63:1:140 in a volume ratio and the soaking time is varied at four stages from 0 to 2 minutes. The longer the soaking time, the more the roughness on the silicon substrate surface is increased. FIG. 1 is a chart showing a relation between soaking time and the roughness of the silicon substrate surface as shown in a concentration of chlorine ion. The silicon substrates with different surface roughness are soaked in a mixture of hydrochloric acid, hydrogen peroxide solution and deionized water at a room temperature for 10 minutes. The mixing ratio of this mixture is approximately 1:1:16.7 in a volume ratio. Then, the silicon substrates are rinsed in deionized water to remove the reagent and then dried by the spin-dry method.

Then, chlorine element in the samples thus obtained is detected by the above total reflection X-ray fluorescence analysis. FIG. 1 shows the relation between the concentration of the above chlorine element and the soaking time in the mixture of nitric acid, hydrofluoric acid and deionized water. As can be seen from the figure, the amount of chlorine is increased in accordance with the soaking time and it can be confirmed that evaluation of the surface roughness is possible. More specifically, the roughness on the silicon surface can be quantitatively evaluated by measuring the amount of chlorine.

The measuring condition of the total reflection X-ray fluorescence analysis at this time is as follows.

| [Condition of total reflection X-ray fluorescence analysis] | |
| --- | --- |
| X-ray | WL$\beta$ (tungsten L$\beta$) |
| X-ray generation condition | Filament current 200 mA Electron acceleration voltage 30 kV |
| X-ray sample incident angle | 0.05° |
| Measuring time | 500 seconds |
| Size of sample | Approximately 1 cm$^2$ |

In addition, evaluation of surface roughness (Ra) by the conventional method using the atomic force microscope (AFM), corresponding to a evaluation result of the present invention, is confirmed. The measuring condition of the AFM is as follows.

Measuring condition by AFM

The silicon substrate surface is measured by AFM in the atmosphere and then centerline average roughness (Ra) is calculated from a profile of its cross section.

EXAMPLE

Figure 3:
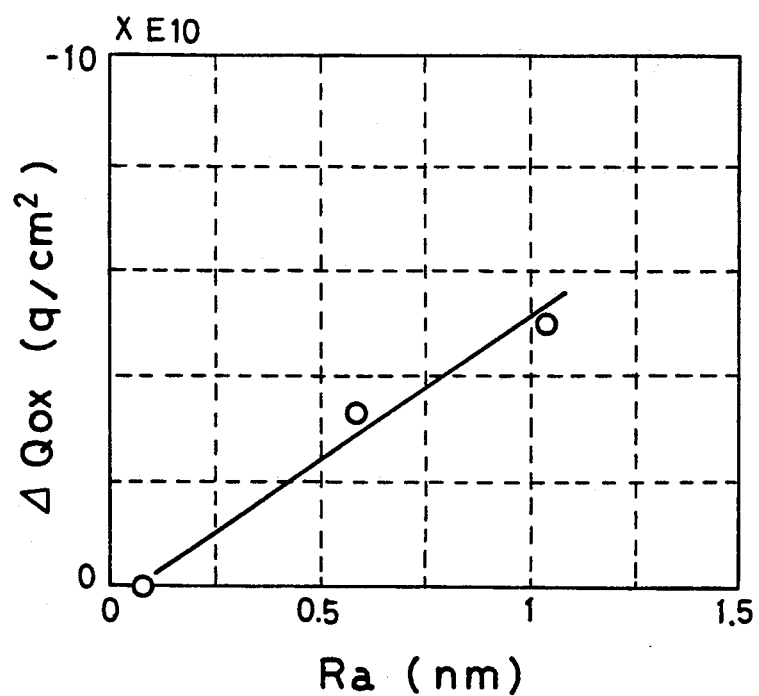
FIG. 3 is a chart showing a relation between an amount of the electric charge in a native oxide film measured by the surface charge analyzer and surface roughness measured by a conventional AFM method.

Three kinds of silicon substrates having different surface roughness are soaked in a mixture of hydrochloric acid (HCl; concentration approximately 30 vol %), hydrogen peroxide solution (H$_2$O$_2$; concentration approximately 30 vol %) and demineralized water (H$_2$O) (its volume ratio is as follows, HCl:H$_2$O$_2$:H$_2$O=1:1:16.7) for ten minutes, then rinsed in water and dried. Then, an amount of the electric charge in a native oxide film is measured by a surface charge analyzer and then surface roughness (central average roughness Ra) is measured by the AFM. FIG. 3 shows a difference ($Q_{OX}$) in the amount of the electric charge in the native oxide film on the basis of the silicon substrate having the smallest Ra. Thus, the relation between Ra and $Q_{OX}$ can be confirmed. More specifically, it is possible to quantatively evaluate the surface roughness by measuring the amount of electric charge in the native oxide film.

The method for measuring the amount of electric charge corresponding to chlorine ion measures the electric charge by the surface charge analyzer. The measuring condition is as follows.

Measuring apparatus of surface charge analyzer

Figure 2:
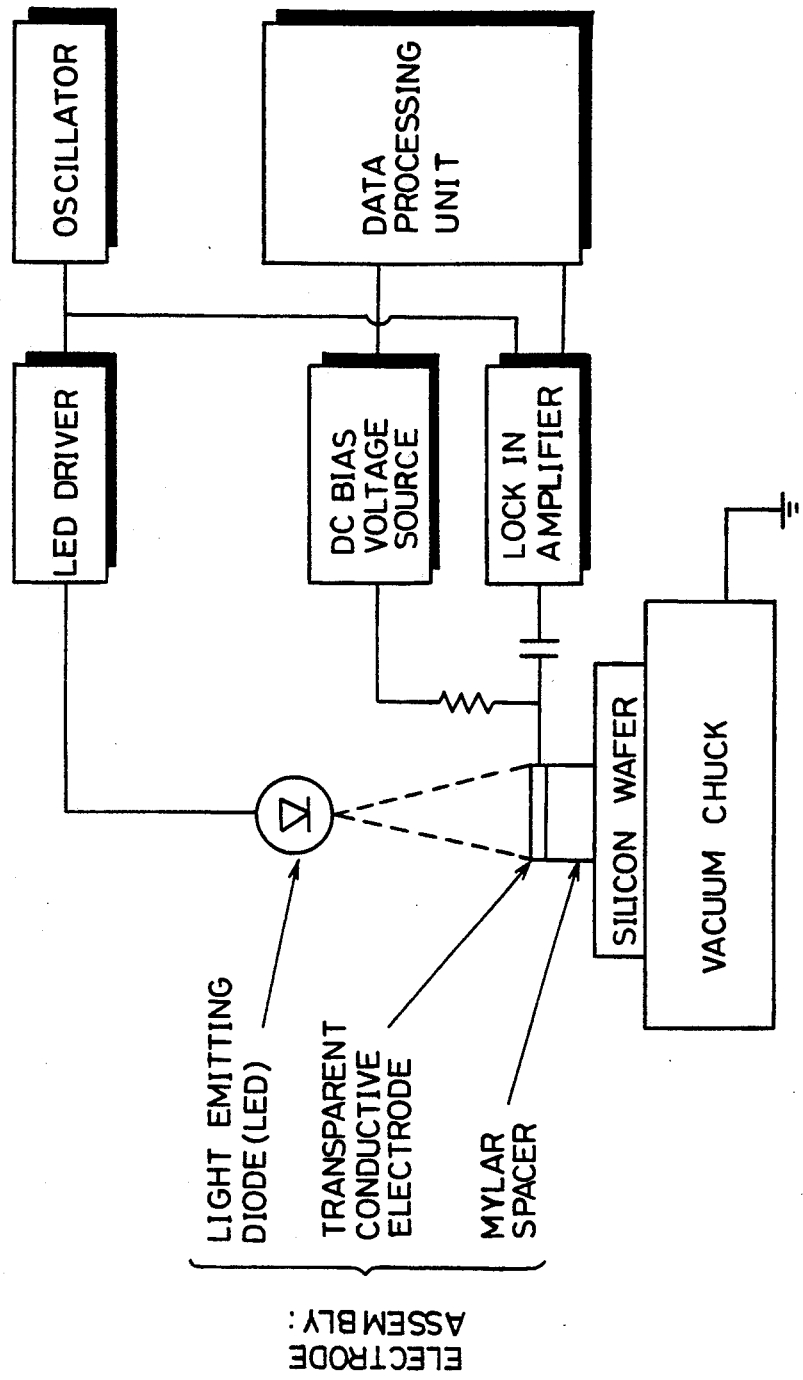
FIG. 2 is a block diagram showing a measuring apparatus used in an surface charge analyzer according to the present invention.

An apparatus used for that measurement is made by Semitest Co. whose block diagram is shown in FIG. 2. The measuring condition is as follows.

| Thickness of mylar spacer | Approximately 12 $\mu$m |
| --- | --- |
| Applied voltage (Variable voltage bias) | 1000 V or more |

-continued

| Size of sample | Approximately 1 cm$^2$ |
| --- | --- |
| Measured value | SPV (surface photovoltage) |

In addition, after the native oxide film, which is formed in mixture of nitric acid and hydrofluoric acid, is removed by hydrofluoric acid, and then soaking in hydrochloric acid and hydrogen peroxide solution, the concentration of chlorine is also considerably increased. Thus, it is found that the concentration of chlorine on the surface is increased regardless of the native oxide film formed by the processing in the mixture of nitric acid and hydrofluoric acid.

The maximum area which can be measured by the conventional method, for example AFM method is $10^{-4}$ cm$^2$ (=100 $\mu$m×100 $\mu$m) because of a limit of the measuring condition and apparatus, so that the whole area is evaluated by only a part of the sample. Meanwhile, according to the method of the present invention, the area of the sample which can be measured is approximately 1 cm$^2$, which is approximately 10000 times as large as that of the conventional method. Therefore, it is possible to evaluate a considerably large area of the sample. More specifically, in the total reflection X-ray fluorescence analysis, the region on the surface which is evaluated is equal to an area of an X-ray detector. In addition, when the amount of the electric charge in the native oxide film is measured by the surface charge analyzer, the region on the surface which is evaluated is equal to an electrode area of the measuring apparatus, which is also approximately 1 cm$^2$.

While only certain presently preferred embodiments have been described in detail, as will be apparent with those skilled in the art, certain changes and modifications can be made without departing from the scope of the invention as defined by the following claims.

What is claimed is:

1. A method for evaluating surface micro roughness of a silicon substrate comprising the steps of:
    soaking the silicon substrate in a mixture of hydrochloric acid of 30 to 40 vol %, hydrogen peroxide solution of 30 to 40 vol % and deionized water whose volume ratio is approximately 1:1:16.7;
    measuring an amount of chlorine element deposited on the silicon surface through the soaking process; and
    evaluating the degree of the micro roughness on the silicon substrate surface by comparing the measured chlorine amount with a known chlorine amount measured for silicon substrates of known surface micro roughness, said known chlorine amounts being obtained by performing said soaking step on said silicon substrates of known surface micro roughness and measuring the chlorine amount of each substrate thereafter.

2. A method for evaluating surface micro roughness of a silicon substrate according to claim 1, wherein the amount of chlorine element is measured by a total reflection X-ray fluorescence analysis or a X-ray micro analyzer.

3. A method for evaluating surface micro roughness of a silicon substrate according to claim 1, wherein the amount of chlorine element is evaluated by measuring an amount of electric charge caused by chlorine ions incorporated into a native oxide film.

4. A method for evaluating surface roughness of a silicon substrate according to claim 3, wherein the amount of electric charge is measured by a surface charge analyzer.

5. A method for evaluating surface micro roughness of a silicon substrate according to claim 1, wherein the soaking step employs a soaking temperature of about 25° C. to about 40° C.

6. A method for evaluating surface micro roughness of a silicon substrate according to claim 1, wherein the soaking step employs a soaking time of about 5 to about 20 minutes.

* * * * *